US010163239B2

United States Patent
Chae

(10) Patent No.: US 10,163,239 B2
(45) Date of Patent: Dec. 25, 2018

(54) COMPUTER-AIDED DIAGNOSTIC APPARATUS AND METHOD BASED ON DIAGNOSTIC INTENTION OF USER

(71) Applicant: SAMSUNG ELECTRONICS CO., LTD., Suwon-si (KR)

(72) Inventor: Seung Chul Chae, Seoul (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 212 days.

(21) Appl. No.: 14/943,107

(22) Filed: Nov. 17, 2015

(65) Prior Publication Data

US 2016/0155227 A1   Jun. 2, 2016

(30) Foreign Application Priority Data

Nov. 28, 2014 (KR) .................. 10-2014-0169018

(51) Int. Cl.
| | |
|---|---|
| *G06T 11/60* | (2006.01) |
| *A61B 8/00* | (2006.01) |
| *A61B 8/08* | (2006.01) |
| *A61B 5/055* | (2006.01) |
| *A61B 6/03* | (2006.01) |
| *A61B 5/00* | (2006.01) |

(52) U.S. Cl.
CPC ............ *G06T 11/60* (2013.01); *A61B 8/4254* (2013.01); *A61B 8/4416* (2013.01); *A61B 8/469* (2013.01); *A61B 8/5223* (2013.01); *A61B 5/055* (2013.01); *A61B 5/7485* (2013.01); *A61B 6/032* (2013.01); *A61B 8/085* (2013.01); *A61B 8/0825* (2013.01)

(58) Field of Classification Search
CPC ..... G06T 11/60; A61B 8/4254; A61B 8/4416; A61B 8/469; A61B 8/5223; A61B 8/0825; A61B 8/085; A61B 5/055; A61B 5/7485; A61B 6/032
See application file for complete search history.

(56) References Cited

U.S. PATENT DOCUMENTS

| | | | |
|---|---|---|---|
| 2008/0072151 A1* | 3/2008 | Song ................. | G06F 3/0481 715/708 |
| 2012/0172726 A1* | 7/2012 | Sakai ................. | A61B 8/00 600/443 |
| 2013/0158397 A1* | 6/2013 | K. ................. | G06F 19/322 600/437 |

(Continued)

OTHER PUBLICATIONS

Tan, Tao, et al. "Computer-aided lesion diagnosis in automated 3-D breast ultrasound using coronal spiculation." IEEE transactions on medical imaging 31.5 (2012): 1034-1042.*

*Primary Examiner* — Shefali D Goradia
(74) *Attorney, Agent, or Firm* — Sughrue Mion, PLLC

(57) ABSTRACT

A computer-aided diagnostic (CAD) apparatus and a CAD method based on the diagnostic intention of a user are provided. The CAD apparatus includes a region of interest (ROI) detector configured to detect an ROI from an image input from a probe, and a probe motion determiner configured to determine a motion of the probe in response to the ROI detector detecting the ROI. The CAD apparatus further includes a diagnostic intention determiner configured to determine a diagnostic intention of a user based on the determined motion of the probe, and a diagnostic intention processor configured to perform a diagnostic procedure based on the determined diagnostic intention of the user.

18 Claims, 12 Drawing Sheets

| PROBE MOTION | EXAMPLES OF PROBE STATE | DESCRIPTIONS |
|---|---|---|
| TURN | TURN | TURN PROBE |
| SAVING MOTION | PUSH | MOVE PROBE ORTHOGONALLY |
| EDITING MOTION | LR SHAKE | SHAKE PROBE LEFT AND RIGHT |
| ZOOMING | FB SHAKE | SHAKE PROBE BACK AND FORTH |
| STATIONARY | STAY | LET PROBE STAY |
| MOVING | MOVE | MOVE PROBE |

| DIAGNOSTIC STATE | PROBE MOTION | DIAGNOSTIC INTENTION |
|---|---|---|
| NO ROI DETECTED | - | - |
| ROI DETECTED AND DISPLAYED | STATIONARY ≥ 2 SECONDS | MEASURE ROI |
| ROI MEASURED | STATIONARY ≥ 1 SECONDS | FREEZE SCREEN |
| SCREEN FROZEN | MOVE | UNFREEZE SCREEN |
| | STATIONARY ≥ 1 SECONDS | DISPLAY ROI MEASUREMENT INFORMATION |
| SCREEN FROZEN AND MEASUREMENT INFORMATION DISPLAYED | SAVING MOTION | SAVE DIAGNOSTIC INFORMATION DISPLAYED ON CURRENT SCREEN |
| | EDITING MOTION | SWITCH SCREEN TO EDIT MODE |
| | MOVING | INITIALIZE SCREEN AND UNFREEZE |
| SCAN | SAVING MOTION | SAVE CURRENT SCREEN |

(56) References Cited

U.S. PATENT DOCUMENTS

| | | | |
|---|---|---|---|
| 2014/0107487 A1 | 4/2014 | Kim et al. | |
| 2015/0087979 A1* | 3/2015 | Zhang | A61B 8/4494 600/440 |
| 2015/0302583 A1* | 10/2015 | Jeon | G06T 7/0016 382/128 |

* cited by examiner

FIG. 4A

| PROBE MOTION | EXAMPLES OF PROBE STATE | DESCRIPTIONS |
|---|---|---|
| TURN | TURN | TURN PROBE |
| SAVING MOTION | PUSH | MOVE PROBE ORTHOGONALLY |
| EDITING MOTION | LR SHAKE | SHAKE PROBE LEFT AND RIGHT |
| ZOOMING | FB SHAKE | SHAKE PROBE BACK AND FORTH |
| STATIONARY | STAY | LET PROBE STAY |
| MOVING | MOVE | MOVE PROBE |

FIG. 4B

| DIAGNOSTIC STATE | PROBE MOTION | DIAGNOSTIC INTENTION |
|---|---|---|
| NO ROI DETECTED | - | - |
| ROI DETECTED AND DISPLAYED | STATIONARY ≥ 2 SECONDS | MEASURE ROI |
| ROI MEASURED | STATIONARY ≥ 1 SECONDS | FREEZE SCREEN |
| SCREEN FROZEN | MOVE | UNFREEZE SCREEN |
| | STATIONARY ≥ 1 SECONDS | DISPLAY ROI MEASUREMENT INFORMATION |
| SCREEN FROZEN AND MEASUREMENT INFORMATION DISPLAYED | SAVING MOTION | SAVE DIAGNOSTIC INFORMATION DISPLAYED ON CURRENT SCREEN |
| | EDITING MOTION | SWITCH SCREEN TO EDIT MODE |
| | MOVING | INITIALIZE SCREEN AND UNFREEZE |
| SCAN | SAVING MOTION | SAVE CURRENT SCREEN |

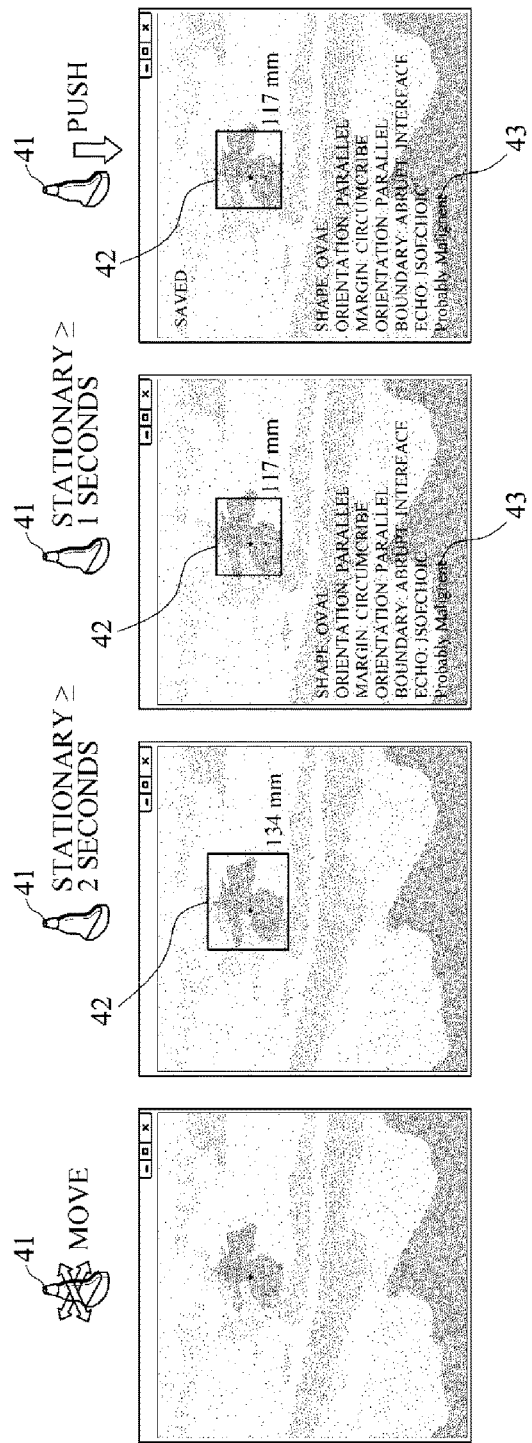

FIG. 6

| DIAGNOSTIC STATE | NUMBER OF INPUT SIGNALS DURING TIME UNIT | DIAGNOSTIC INTENTION |
|---|---|---|
| NO ROI DETECTED | - | - |
| ROI DETECTED AND DISPLAYED | 1 | MEASURE ROI |
| ROI MEASURED AND DISPLAYED | 1 | SWITCH CURRENT SCREEN TO EDIT MODE |
| | 2 | SAVE DIAGNOSTIC INFORMATION |
| | 3 | INITIALIZE SCREEN AND ENTER SCAN MODE |
| DIAGNOSTIC INFORMATION EDITED | 2 | SAVE EDITED DIAGNOSTIC INFORMATION |
| | 3 | INITIALIZE SCREEN AND ENTER SCAN MODE |
| SCAN | 2 | SAVE CURRENT SCREEN |

COMPUTER-AIDED DIAGNOSTIC APPARATUS AND METHOD BASED ON DIAGNOSTIC INTENTION OF USER

CROSS-REFERENCE TO RELATED APPLICATION

This application claims priority from Korean Patent Application No. 10-2014-0169018, filed on Nov. 28, 2014, in the Korean Intellectual Property Office, the disclosure of which is incorporated herein by reference in its entirety.

BACKGROUND

1. Field

Apparatuses and methods consistent with exemplary embodiments relate to a computer-aided diagnostic (CAD) apparatus and a CAD method based on a diagnostic intention of a user.

2. Description of the Related Art

By using a general ultrasound diagnostic device, an examiner can detect a lesion by moving a probe over and thus scanning a suspicious area of a patient's body. A probe is a device that emits ultrasound waves directed into the human body, and generates images from reflected ultrasound waves from the body that it receives. Once a lesion is detected in the images sent by the probe, the examiner looks for an image that shows the lesion most clearly, freezes the image to inspect the lesion more carefully, inputs diagnostic information, and then saves the input information for future diagnosis. That is, when information, which is obtained in real time by moving the probe over the body of the patient, is displayed on a display screen, the examiner, such as an expert in ultrasound image interpretation and diagnosis, may do a visual search for a lesion in a suspicious area in the displayed ultrasound images (SCAN step); freeze the screen to further inspect the area of interest (FREEZE step); measure the size and boundary of the ROI if determined to be a lesion (MEASURE step); make an annotation about the lesion's location along with other information regarding the measured lesion and save the annotation (SAVE step); unfreeze the screen to continue to scan; and repeat the aforesaid operations. As such, the examiner may manually manipulate the CAD apparatus depending on the operation, and may have difficulty focusing his attention.

SUMMARY

Exemplary embodiments address at least the above problems and/or disadvantages and other disadvantages not described above. Also, one or more exemplary embodiments are not required to overcome the disadvantages described above, and an exemplary embodiment may not overcome any of the problems described above.

According to an aspect of an exemplary embodiment, there is provided a computer-aided diagnostic (CAD) apparatus including a region of interest (ROI) detector configured to detect an ROI from an image input from a probe, a probe motion determiner configured to determine a motion of the probe in response to the ROI detector detecting the ROI, a diagnostic intention determiner configured to determine a diagnostic intention of a user based on the determined motion of the probe, and a diagnostic intention processor configured to perform a diagnostic procedure based on the determined diagnostic intention of the user.

The probe motion determiner may be configured to determine the motion of the probe based on consecutive images input from the probe.

The probe motion determiner may be configured to calculate a similarity between the input consecutive images, and determine the motion of the probe based on the calculated similarity.

The probe motion determiner may be configured to determine the motion of the probe, using one or more sensors that are mounted on the probe, the one or more sensors including at least one among an acceleration sensor, a gyro sensor, and a motion sensor.

The diagnostic intention determiner may be configured to determine the diagnostic intention of the user corresponding to the determined motion of the probe that are included in intention-based classification information.

The CAD apparatus may further include an intention information storage configured to store the intention-based classification information that maps motions of the probe to diagnostic intentions of the user.

The diagnostic intention of the user may be to perform one among scanning another image with the probe, measuring the ROI, freezing a screen, editing diagnostic information, and saving the diagnostic information.

The diagnostic intention processor may include an ROI measurer configured to measure the detected ROI in response to the determined diagnostic intention of the user being to perform measuring the ROI, a screen display configured to freeze the screen and display a result of the measuring the ROI on the frozen screen, in response to the determined diagnostic intention of the user being to perform freezing the screen, and a diagnostic information storage configured to store the diagnostic information that is displayed on the screen in response to the determined diagnostic intention of the user being to perform saving the diagnostic information.

The screen display may be further configured to in response to the determined diagnostic intention of the user being to perform editing the diagnostic information, switch the screen to an edit mode, and in response to the determined diagnostic intention being to perform scanning the other image, initialize the frozen screen and display the other image input from the probe on the initialized screen.

The motion of the probe may include at least one among being stationary, a moving motion, an editing motion, and a saving motion.

The diagnostic intention determiner may be configured to determine that the diagnostic intention of the user is to perform measuring the ROI in response to the determined motion of the probe including being stationary during a first time unit from a moment the ROI is detected.

The diagnostic intention determiner may be configured to determine that the diagnostic intention of the user is to perform freezing a screen in response to the determined motion of the probe including being stationary during a second time unit from a moment the ROI is measured.

The diagnostic intention determiner may be configured to in response to the determined motion of the probe including the moving motion during a third time unit from a moment the screen is frozen, determine that the diagnostic intention of the user is to perform scanning another image with the probe, and in response to the determined motion of the probe including being stationary during the third time unit from the moment the screen is frozen, determine that the diagnostic intention of the user is to perform displaying a result of the measuring the ROI on the frozen screen.

The diagnostic intention determiner may be configured to in response to the determined motion of the probe including the editing motion during the third time unit from the moment the screen is frozen, determine that the diagnostic intention of the user is to perform editing diagnostic information, and in response to the determined motion of the probe including the saving motion during the third time unit from the moment the screen is frozen, determine that the diagnostic intention of the user is to perform saving the diagnostic information.

According to an aspect of another exemplary embodiment, there is provided a computer-aided diagnostic (CAD) method including detecting a region of interest (ROI) from an image input from a probe, determining a motion of the probe in response to the detecting the ROI, determining a diagnostic intention of a user based on the determined motion of the probe, and performing a diagnostic procedure based on the determined diagnostic intention of the user.

The diagnostic intention of the user may be to perform one among scanning another image with the probe, measuring the ROI, freezing a screen, editing diagnostic information, and saving the diagnostic information.

The performing the diagnostic procedure may include measuring the detected ROI in response to the determined diagnostic intention of the user being to perform measuring the ROI, freezing the screen and displaying a result of the measuring the ROI on the screen, in response to the determined diagnostic intention of the user being to perform freezing the screen, and storing the diagnostic information that is displayed on the screen in response to the determined diagnostic intention of the user being to perform saving the diagnostic information.

The performing the diagnostic procedure may further include in response to the determined diagnostic intention of the user being to perform editing the diagnostic information, switching the screen to an edit mode, and in response to the determined diagnostic intention being to perform scanning the other image, initializing the frozen screen and displaying the other image input from the probe on the initialized screen.

According to an aspect of another exemplary embodiment, there is provided a computer-aided diagnostic (CAD) apparatus including a region of interest (ROI) detector configured to detect an ROI from an image input from a probe, an input signal receiver configured to receive one or more input signals from an interface, a diagnostic intention determiner configured to determine a diagnostic intention of a user based on the received one or more input signals, and a diagnostic intention processor configured to perform a diagnostic procedure based on the determined diagnostic intention of the user.

The diagnostic intention determiner may be configured to determine the diagnostic intention of the user based on at least one among a number, types, and combination patterns of the one or more input signals.

BRIEF DESCRIPTION OF THE DRAWINGS

The above and/or other aspects will be more apparent by describing exemplary embodiments with reference to the accompanying drawings, in which:

FIG. 4A is a table showing probe motions, according to an exemplary embodiment;

FIG. 4B is a table showing intention-based classification information mapping according to probe motions, according to an exemplary embodiment;

FIG. 4C is a diagram illustrating changes in a screen according to a user's diagnostic intention, according to an exemplary embodiment;

FIG. 6 is a table showing intention-based classification according to an input signal from a user, according to an exemplary embodiment;

DETAILED DESCRIPTION OF EXEMPLARY EMBODIMENTS

Figure 1:
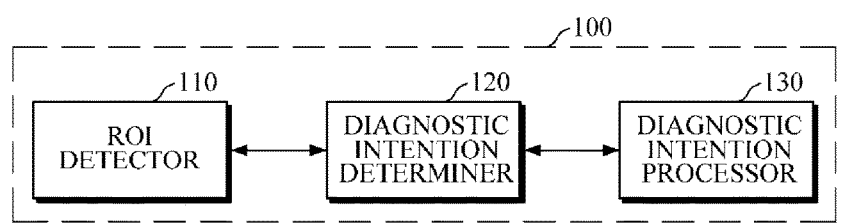
FIG. 1 is a block diagram illustrating a computer-aided diagnostic (CAD) apparatus, according to an exemplary embodiment.

Exemplary embodiments are described in greater detail with reference to the accompanying drawings.

Exemplary embodiments of the present disclosure may be diversely modified. Accordingly, exemplary embodiments are illustrated in the drawings and are described in detail in the detailed description. However, it is to be understood that the present disclosure is not limited to a specific exemplary embodiment, but includes all modifications, equivalents, and substitutions without departing from the scope and spirit of the present disclosure. Also, well-known functions or constructions may not be described in detail because they would obscure the disclosure with unnecessary detail.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters. Hereinafter, it is understood that expressions such as "at least one of," when preceding a list of elements, modify the entire list of elements and do not modify the individual elements of the list.

Hereinafter, exemplary embodiments of a computer-aided diagnostic (CAD) apparatus and a CAD method based on a user's intention for diagnosis will be described in detail with reference to appended drawings.

The CAD apparatus according to the exemplary embodiments may be an apparatus used to classify ultrasound images obtained by a probe or medical images obtained using various techniques, such as computed tomography (CT) or magnetic resonance imaging (MRI) techniques. Herein, for convenience of explanation, an apparatus for classifying ultrasound images obtained by a probe will be described.

FIG. 1 is a block diagram illustrating a CAD apparatus 100, according to an exemplary embodiment.

Referring to FIG. 1, the CAD apparatus 100 includes a region of interest (ROI) detector 110, a diagnostic intention determiner 120, and a diagnostic intention processor 130.

The ROI detector 110 receives ultrasound images. The ultrasound images are obtained by a probe as it scans an area of interest. The ultrasound images from the probe may be received in real time in units of frames.

In addition, in response to receiving the images, the ROI detector 110 detects an ROI in a currently received image by applying an object detection algorithm thereto. Here, the ROI may be an area from the image where an object of interest that a user wants to analyze is located. The object of interest may include, for example, a lesion or a fetus's head, fingers, and toes, but is not limited thereto. In this example, the ROI indicates an area suspected of containing a lesion. The object detection algorithm may be, for example, Ada-Boost, Deformable Part Models (DPM), a deep neural network (DNN), a convolutional neural network (CNN), or spare coding, and is not limited thereto. One or more algorithms may be applied by taking into consideration the capabilities of the CAD apparatus 100, purpose of diagnosis, diagnostic time period, or the like.

When an ROI is not detected in the current image, the ROI detector 110 may receive a subsequent image from the probe and repeat the ROI detection process in the subsequently received image.

If an ROI is detected in the subsequently received image, the diagnostic intention determiner 120 responds by inferring the user's diagnostic intention regarding the diagnostic procedures the user wishes to carry out on the detected ROI.

For example, the diagnostic intention determiner 120 may determine the diagnostic intention based on a motion of the probe or a user input signal received through a connected interface. In addition, the diagnostic intention determiner 120 may determine the user's diagnostic intention using various methods, such as detecting eye movement or gaze direction.

Here, the user's diagnostic intention may indicate various actions including scanning a suspicious area using a probe, measuring a detected ROI, freezing a displayed screen, editing diagnostic information, and saving the diagnostic information. However, the diagnostic intention is not limited thereto, such that the diagnostic intention may include only some of the aforementioned actions or add other actions (e.g., the type of diagnosed disease, the purpose of diagnosis, and the user's proficiency and experience) according to the computing performance of the CAD apparatus 100. For example, the screen freeze operation may be omitted or simplified; or the ROI measurement operation may be broken down into a number of procedures such as ROI size measurement, feature extraction, and a malignancy/benignity classification.

The diagnostic intention processor 130 performs diagnostic procedures that correspond to the determined diagnostic intention of the user.

For example, if the determined diagnostic intention is to measure the ROI, feature information about the detected ROI is extracted, and then classification on whether it is malignant or benign is carried out using the extracted feature information. In addition, if the user's diagnostic intention is to freeze the displayed screen, the current displayed screen is frozen, and a measurement result of the ROI may be displayed on the current screen. Furthermore, if the determined diagnostic intention is to save diagnostic information, then the action is performed; if the diagnostic intention is to edit the diagnostic information, then the current screen may be switched to edit mode; if the determined diagnostic intention of the user is to scan an image, the current screen is initialized, and a subsequent image input from the probe may be output onto the screen.

Figure 2:
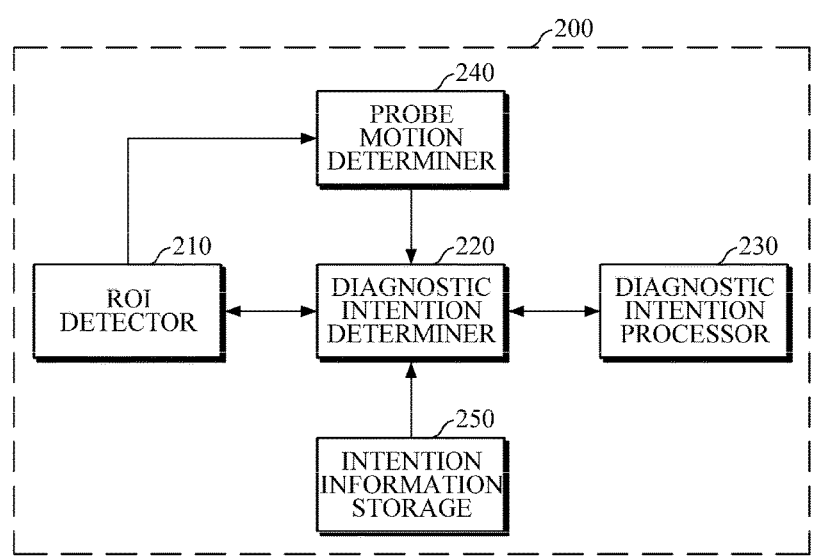
FIG. 2 is a block diagram illustrating a CAD apparatus, according to another exemplary embodiment.

FIG. 2 is a block diagram illustrating a CAD apparatus 200, according to another exemplary embodiment.

Referring to FIG. 2, the CAD apparatus 200 includes an ROI detector 210, a diagnostic intention determiner 220, a diagnostic intention processor 230, a probe motion determiner 240, and an intention information storage 250.

The ROI detector 210 receives an image input from a probe, and examines it for any ROI that may be present. The ROI detector 210 may detect an ROI using any appropriate object detection algorithm as described above. When no ROI is detected from the current image, the ROI detector 210 may iteratively receive an image and examine it for any ROI.

When an ROI is detected, the probe motion determiner 240 determines a motion of the probe, based on the diagnostic intention of the user that is determined. The motion of the probe may be defined as 'Turn (a turning motion),' 'Push (a saving motion),' 'LR Shake (an editing motion),' 'FB Shake (a zooming motion),' 'Stay (being stationary),' and 'Move (moving),' but some may be omitted or other motions may be added.

In an exemplary embodiment, the probe motion determiner 240 may determine the motion of a probe by analyzing consecutive images from the probe. By analyzing any locational changes of a feature across consecutively input images, the probe motion determiner is able to determine whether the probe is stationary or in motion, and if the probe is indeed determined as being in motion, the probe motion determiner 240 determines the direction and speed in which the probe is moving. In such cases, the degree of similarity among consecutive images is calculated, and if the obtained degree is greater than a threshold (e.g., 95%), the probe motion determiner 240 may determine that the probe is in stationary. In this regard, as the probe motion may vary according to the user, the threshold may be set differently for each user.

In another exemplary embodiment, the probe motion determiner 240 may use sensors installed inside the probe (e.g., an acceleration sensor, a gyro sensor, and motion sensor, etc.) to determine whether the probe is stationary or in motion, and, if in motion, determine its direction and speed. In addition, an image capturing device, such as a motion camera or a depth camera, is installed at a location inside the CAD apparatus 200 to capture the probe motion, and the probe motion determiner 240 may determine the probe motion by analyzing input images from the image capturing device. To avoid performance degradation, the probe motion determiner 240 may determine the probe motion only after an ROI has been detected in a current image.

The diagnostic intention determiner 220 determines what the user's diagnostic intention is based on any probe motion that is registered in the current diagnostic state. The diagnostic intention determiner 220 is able to collect information regarding the operational state of the CAD apparatus 200 and then determine the current diagnostic state of the CAD apparatus. For example, the diagnostic intention determiner 220 may determine whether the probe is obtaining ultrasound images and thus image scanning is in progress, whether an ROI has been detected by an object detection algorithm, whether the ROI has been measured, or whether the screen is in a freeze state.

In addition, when probe motion is determined to correspond to a diagnostic intention, the diagnostic intention determiner 220 may determine the user's diagnostic intention as being the diagnostic intention that matches the intention-based classification information stored in the intention information storage 250. The intention-based classification information maps probe motions that have been matched to the user's diagnostic intentions and may be stored beforehand in various forms, such as a table, ontologies, logical formulas, etc.

The diagnostic intention processor 230 performs diagnostic procedures corresponding to the determined diagnostic intention of the user.

Figure 3:
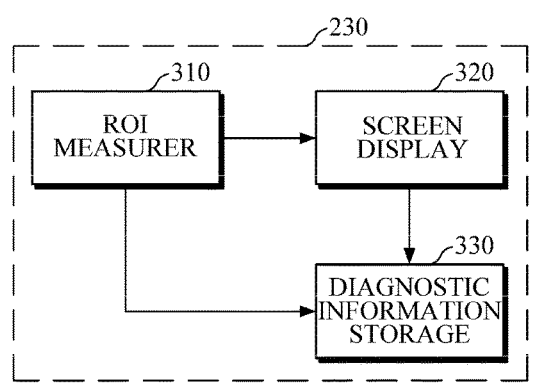
FIG. 3 is a block diagram illustrating a diagnostic intention processor of the CAD apparatus in FIG. 2.

FIG. 3 is a block diagram illustrating the diagnostic intention processor 230 of the CAD apparatus in FIG. 2. Referring to FIG. 3, the diagnostic intention processor 230 includes an ROI measurer 310, a screen display 320, and a diagnostic information storage 330.

When the user's diagnostic intention is determined, based on the probe motion, as an ROI is being measured, then the ROI measurer 310 measures the ROI, whereby such measuring action is a part of the diagnostic process. Measurement of ROI may be performed in the background.

The ROI measurer 310 may measure the size of detected ROI, extract information regarding any features of the ROI, classify the ROI as being either malignant or benign using the extracted feature information, after which the ROI measurer 310 may finally generate ROI measurement information.

The feature information may contain data regarding the features of a lesion, such as its shape, echo pattern, orientation, boundary, texture, and intensity; the information may also contain characteristics of the lesion that are in accordance with lexicon classifications (Breast Imaging and Data System (BI-RADS) or Liver Imaging Reporting and Data System (LI-RADS)). So for example, an ROI measurement result generated may show a lesion as having an oval shape with a 15 mm major axis and 5 mm minor axis, and an inclination of 45 degree; the information regarding the characteristics of the lesion may also be shown, such as an irregular boundary, shadowing, and a 45% probability of being benign.

The screen display 320 outputs a current image that is being received from the probe to the display screen. In addition, when an ROI is detected from the current image, the screen display 320 may visually indicate the ROI, in the current image, using information about the ROI (e.g., location and size of the ROI). For example, the screen display 320 may make a visual indication of the ROI at its position in the current image with colored markers (e.g. bounding box, circle, ellipse, cross) or by adjusting the style and thickness of the lines so that the ROI can be visually recognized.

In addition, upon commencement of ROI measurement, if it is determined that the user's diagnostic intention is to freeze the screen, then the screen display 320 may freeze the current screen image and output, to the display screen, diagnostic information that contains the measurement information of ROI.

Moreover, if the diagnostic information that contains the ROI's measurement information is output to the current screen and then it is determined that the user's diagnostic intention is to edit the diagnostic information, the screen display 320 may switch the current screen to edit mode, thus allowing the user to make any changes to the diagnostic information.

In this case, the user may edit the diagnostic information by utilizing various input interfaces mounted on the CAD apparatus 200, such as a keyboard, a touch panel, a mouse or a probe, wherein the diagnostic information may include, for example, the location, size, and measurement information of the ROI. To enable the user the use of both hands during the diagnostic process, such as manipulation of a probe, the CAD apparatus 200 may feature speech recognition technology, allowing the user to edit the diagnostic information by speech. There are a variety of well-known voice recognition technologies that can be utilized, and thus descriptions thereof will be omitted.

Further, if it is determined that the user's diagnostic intention is image scanning by which a new image is input, the screen display 320 may initialize the current screen and output a subsequent input image from the probe to the display.

If the measurement of ROI is complete and then it is determined that the user's diagnostic intention is to save the diagnostic information, the diagnostic information storage 330 saves the information that contains the image and measurement information which are currently being displayed on screen.

FIG. 4A is a table showing probe motions, according to an exemplary embodiment. FIG. 4B is a table showing intention-based classification information mapping according to probe motions, according to an exemplary embodiment. FIG. 4C is a diagram illustrating changes in a screen according to a user's diagnostic intention, according to an exemplary embodiment.

The diagnostic procedures based on a user's diagnostic intention will be described with reference to FIG. 2 and FIGS. 4A to 4C.

As shown in FIG. 4A, motions of a probe may be initially defined as turning, editing motion, zooming, being stationary, and moving, but a probe's motions are not limited thereto. The probe's motions may be set to match user's manipulations of the probe or probe states, for example, 'Turn (a turning motion),' 'Push (a saving motion),' 'LR Shake (an editing motion),' 'FB Shake (a zooming motion),' 'Stay (being stationary),' and 'Move (moving),' and the like.

FIG. 4B is a table showing an example of intention-based classification information stored in the intention information storage 250, where intention-based classification information is defined by mapping probe motions that have been matched to the user's diagnostic intentions. In this case, as shown in the table, the intention-based classification information may be defined by mapping each probe motion that has been matched to a user's diagnostic intention for each diagnostic state. The diagnostic states may be classified into one or more sub-states depending on the diagnostic procedure, such as detection of ROI, display of ROI, measurement of ROI, screen freezing, display of diagnostic or measurement information, and image scanning. However, as described above, some of the aforementioned procedures may be omitted or new procedures may be added thereto, and thus the diagnostic states may be defined differently.

Referring back to FIGS. 2 and 4B, the probe motion determiner 240 continuously determines the motions of the probe after an ROI has been detected from a current image.

From the moment the detected ROI is displayed on the screen, the diagnostic intention determiner 220 registers all probe motions that have been occurred during a time frame (e.g., 2 seconds), which may be referred to as the first time unit. If the probe has remain stationary, lingering on the ROI during the time frame, the diagnostic intention determiner 220 may determine that the user's diagnostic intention is to measure the ROI with reference to the intention-based classification information.

The diagnostic intention processor 230 may measure the ROI according to the user's diagnostic intention and then create measurement information, such as information regarding the ROI's features and classification of malignancy or benignity.

If the user has moved the probe before the end of the first time unit, the diagnostic intention determiner 220 may determine that the user's diagnostic intention is to scan the image.

In response its determination that the user's diagnostic intention is to scan an image, the diagnostic intention processor 230 may initialize the current screen and output new images that are fed to the screen in real-time as the probe moves.

In addition, from the moment the ROI measurement procedure has started, the diagnostic intention determiner 220 registers all probe motions that occur during another time frame (e.g., 2 seconds), which may be referred to as a second time unit. If the probe has remained stationary during the second time unit, the diagnostic intention determiner 220 may determine that the user's diagnostic intention is to freeze the screen, and may thus display diagnostic information to observe in detail the ROI.

Accordingly, the diagnostic intention processor 230 may freeze the screen and output to the screen the diagnostic information that contains the measurement information about the measured ROI.

At this time, the second time unit may be divided into two intervals and the user's intention during each interval is determined as either freezing the screen or displaying diagnostic information according to the probe motion that occurs during the interval. If the screen is frozen according to the user's diagnostic intention determined during the first interval (e.g., 1 second) and thereafter the probe's motion during the following interval (e.g., 1 second) is determined as one of moving or saving, it is accordingly determined that the diagnostic intention of a user is to scan the image or save diagnostic information.

At this time, the diagnostic intention processor 230 may either initialize the current screen or immediately save the diagnostic information depending on the user's diagnostic intention without outputting the diagnostic information to the screen in a freeze state.

If measuring the ROI takes a longer amount of time that that afforded in the first and second time units, only some features of the ROI that can be measured before the end of the second time unit, say, the size of the ROI, is measured, and then the measurement result is displayed. The other measurements of the ROI may be performed while the screen is in a freeze state, and the measurement results are sequentially displayed on the screen.

In addition, if, while the diagnostic information is being displayed on the screen, the probe has remained stationary during a third time unit (e.g., 1 second), the diagnostic intention determiner 220 may determine that the user's diagnostic intention is to automatically save the diagnostic information. In addition, if the user pushes the probe orthogonally during the third time unit, the diagnostic intention determiner 220 may determine that the probe's motion is one of saving as, and that the user's diagnostic intention is to manually save the diagnostic information.

At this time, the diagnostic intention processor 230 stores diagnostic information according to the user's diagnostic intention, and may further store information as to whether the diagnostic information is automatically or manually saved.

In addition, when it is determined that the diagnostic information is to be edited while being displayed on the screen, the user can shake the probe left and right before the end of the third time unit, so that the probe motion can be determined as an editing motion. Then, the diagnostic intention determiner 220 determines that the diagnostic intention of the user is to edit the diagnostic information, to which the diagnostic intention processor 230 switches the current screen to edit mode according to the user's diagnostic intention.

The user may enable the probe motion to be determined as a moving motion in each diagnostic state by moving the probe at any time before each unit time has elapsed. Consequently, the diagnostic intention determiner 220 may determine that the diagnostic intention of the user is to scan an image, and the diagnostic intention processor 230 may initialize the current screen and output a new input image to the screen.

Here, the first time unit, the second time unit, and the third time unit may be appropriately set according to the performance, purpose of diagnosis, type of disease being targeted, and the proficiency of the user with regard to using the CAD apparatus. For example, a computer with low performance takes a relatively longer period of time to measure the ROI, and hence the second time unit, whose length is measured the moment ROI measurement starts, may be set to have a long time frame in proportion to the time taken for the ROI measurement. A user with limited proficiency may take a substantial amount of time to analyze an image and diagnostic information displayed on the screen, and thus the third time unit may be set to be relatively long, during which whether to save or edit the diagnostic information is determined.

FIG. 4C shows, starting from the illustration on the far left, changes in the screen according to the user's diagnostic intention from the moment an image is received to the moment the diagnostic information is saved.

Referring to FIG. 4C, an image received from a probe 41 that the user is moving is output to the screen, and an ROI is detected, as seen in the illustration on the far left.

Thereafter, a bounding box 42 that indicates a detected ROI may be output to the screen. If the user does not move the probe 41 for 2 or more seconds because of the detection of the ROI, the ROI measurement procedure may start, as seen in the second illustration from the left.

If the user does not move the probe for 1 or more seconds after the procedure, measurement information 43 may be displayed at the bottom of the screen, as seen in the third illustration from the left.

Then, when the user pushes the probe 41 with an intention to save the diagnostic information, the diagnostic information 42 and 43 on the current screen is saved, to which the message "SAVED" may be output at the top of the screen, as seen in the illustration on the far right.

Figure 5:
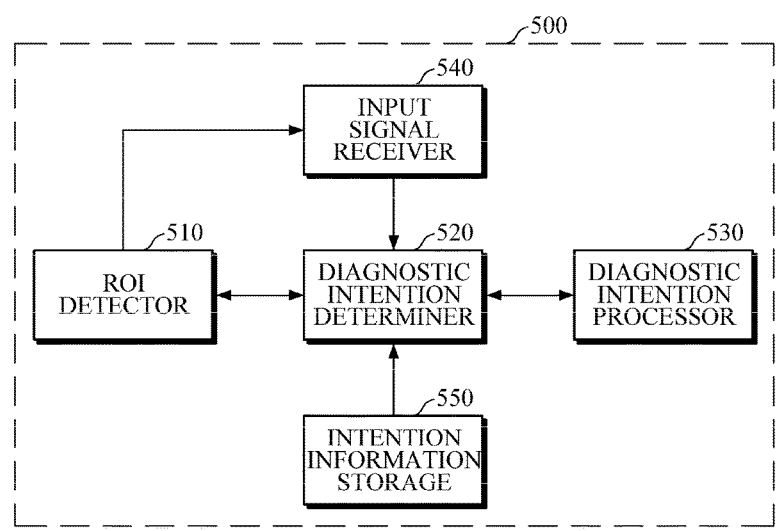
FIG. 5 is a block diagram illustrating a CAD apparatus, according to another exemplary embodiment.

FIG. 5 is a block diagram illustrating a CAD apparatus 500, according to another exemplary embodiment. FIG. 6 is a table showing intention-based classification according to an input signal from a user, according to an exemplary embodiment.

Referring to FIG. 5, the CAD apparatus 500 includes an ROI detector 510, a diagnostic intention determiner 520, a diagnostic intention processor 530, an input signal receiver 540, and an intention information storage 550.

The CAD apparatus 500 of FIG. 5 is another example of the CAD apparatuses 100 and 200 of FIGS. 1 and 2, and it will be construed that components with the same name perform substantially the same function. Therefore, hereinafter, descriptions will be provided with focus on functions that have not been redundantly described.

As described above, the ROI detector 510 receives an image from a probe, and detects an ROI from the currently received image by applying an object detection algorithm.

The input signal receiver 540 receives a user's input signal via an interface. The interface may be, for example, a switch, a button, a trackball, a jog shuttle, a joystick, or the like, which is connected to the CAD apparatus 500, allowing the user to manipulate the CAD apparatus 500 using a his or her body part that is not already engaged in manipulating the probe. In addition, the interface may include a wearable signal generating device in the form of a headband or glasses.

The diagnostic intention determiner 530 determines the diagnostic intention of the user based on the user's input signals, the number of input signals per time unit, types of input signals, a pattern by combining the two, etc., which the input signal receiver 540 has received.

In addition, the diagnostic intention determiner 530 may determine the user's diagnostic intention according to the input signal by utilizing the intention-based classification information stored in the intention information storage 550.

The intention-based classification information is information that maps the user's diagnostic intention with at least one of the following: the predefined number of input signals, type of input signals, and a combination pattern, and it may be stored in various forms, such as tables, logic formulas, or complex ontologies.

The intention-based classification information may be information that maps diagnostic intentions with a variety of signals that are generated as any interface, for example, a jog shuttle or a joystick, is manipulated. For example, a forward push signal, a backward push signal, a left push signal, and a right push signal of a jog shuttle may be mapped with measuring of ROI, screen freezing, saving of diagnostic information, and editing of diagnostic information, respectively, and a shake signal may be mapped with image scanning in which the screen is initialized and a new image is received.

In another example, as shown in FIG. 6, the intention-based classification information may be information that maps the diagnostic intention with the number of input signals being input during a time unit, regardless of the type of an interface.

In yet another example, the intention-based classification information may be information generated by mapping the diagnostic intentions that have been matched to patterns by combining signals input from two or more interfaces, such as a jog shutter (controlled with the left hand) and a switch (controlled with the left foot), patterns by combining types of two or more interfaces, the number of signals input during a time unit, and the like. For example, a switch signal input after detection of the ROI may be matched to the ROI measurement, and each control signal for the jog shuttle after measurement of the ROI may be matched to screen freezing, saving of diagnostic information, editing of diagnostic information, and image scanning.

The diagnostic intention processor 530 performs a diagnostic procedure that corresponds to the user's diagnostic intention, which was determined based on the input signal from the user and with reference to the intention-based classification information, as described above.

FIG. 6 is a diagram illustrating a table showing intention-based classification information that indicates diagnostic intentions of a user, which have been defined according to the number of input signals of each diagnostic state.

An exemplary embodiment of determining a user's diagnostic intention based on the number of input signals from an input device will be described with reference to FIG. 6.

If a single input signal is received during a time unit via an input device while the detected ROI is displayed on screen, the diagnostic intention determiner 520 may determine that the user's diagnostic intention is to measure the detected ROI. At this time, the ROI measurement procedure may be broken down into several stages, such as measurement of a size of ROI, extraction of feature information, and malignancy/benignity classification, and the like.

If the diagnostic intention determiner 520 receives no input signal or receives three input signals from the user during a time unit, the diagnostic intention determiner 520 may determine that the user's diagnostic intention is image scanning, by which the current screen is initialized and the next input image is received.

In addition, if the diagnostic intention determiner 520 receives a single input signal from the input device during the time unit while the diagnostic information that contains the ROI measurement information is being displayed on the screen, the diagnostic intention determiner 520 may determine that the user's diagnostic intention is to edit the diagnostic information.

Further, if the diagnostic intention determiner 520 receives two consecutive input signals during the time unit while the diagnostic information displayed on the screen is in edit mode, the diagnostic intention determiner 520 may determine that the user's diagnostic intention is to save the diagnostic information.

In addition, once the user considers the observance of the current ROI to be pointless, the user may input three consecutive input signals within the time unit, and thereby the current screen is initialized and the user can receive a new input image from the probe.

At this time, the time unit may be set differently according to the performance of the CAD apparatus 230, the purpose of diagnosis, the type of disease being targeted, and the proficiency of the user with regard to using the CAD apparatus. In addition, the time unit may be set differently according to diagnostic state.

Figure 7:
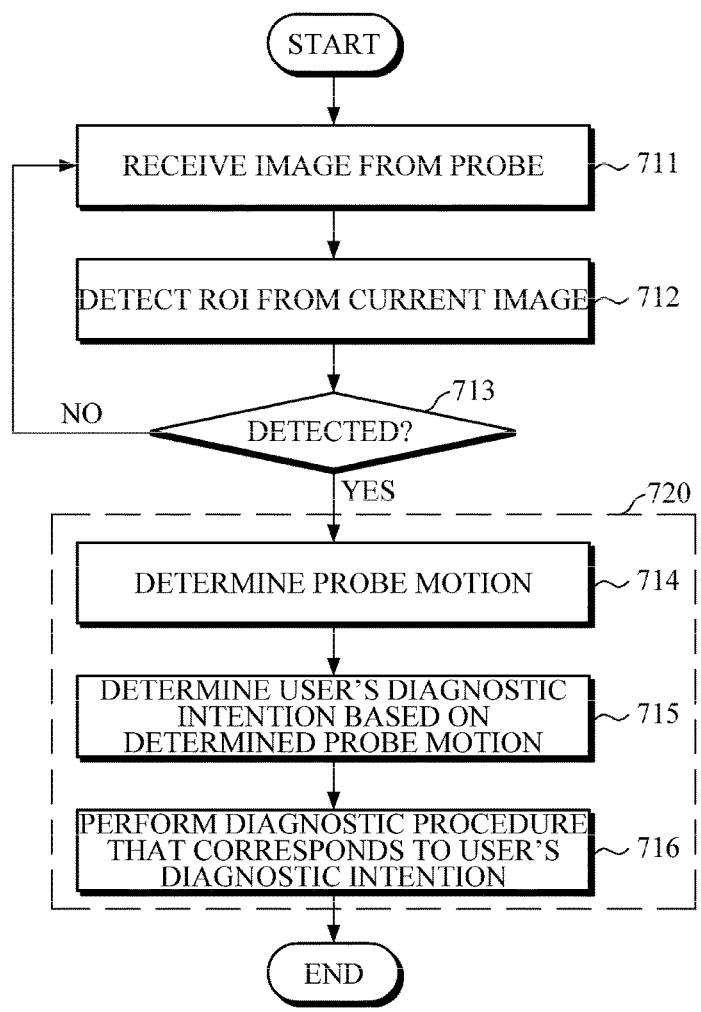
FIG. 7 is a flowchart illustrating a CAD method, according to an exemplary embodiment.

FIG. 7 is a flowchart illustrating a CAD method, according to an exemplary embodiment.

FIG. 7 is an example of the CAD method performed by the CAD apparatus 200 of FIG. 2 based on a probe motion.

In operation 711, the CAD apparatus 200 receives an image from a probe.

In operation 712, the CAD apparatus 200 detects or scans for an ROI from the received current image. At this time, the CAD apparatus 200 may scan for the ROI by applying any of the various object detection algorithms to the current image that are suitable to the computing performance of the CAD apparatus 200. Examples of the object detection algorithms may include AdaBoost, a DPM, a DNN, a CNN, and spare coding.

In operation 713, the CAD apparatus 200 determines whether an ROI is detected from the received current image. If the CAD apparatus 200 fails to detect an ROI from the received current image, the CAD apparatus 200 returns to operation 711, in which the CAD apparatus 200 receives another image from the probe. If the CAD apparatus 200 successfully detects an ROI from the newly-received current image, the CAD apparatus 200 continues in operation 714.

In operation 714, the CAD apparatus 200 determines the motion of the probe. For example, the CAD apparatus 200 may calculate the similarity among the consecutive images, and determine the motion of the probe based on the calculated similarity. If the calculated similarity is greater than a threshold, the probe motion may be determined as being stationary. Otherwise, the probe motion may be determined as moving.

In another example, data about an operational state, referred to as operational data, of the probe may be collected from various sensors mounted on the probe, such as an acceleration sensor, a gyro sensor, and a motion sensor, and the probe motion can be determined based on the collected operational data. Alternatively, the probe motion may be determined using various methods, e.g., analysis of images captured of the movement of the probe.

In operation 715, the CAD apparatus 200 determines the diagnostic intention of the user based on the determined probe motion. The user's diagnostic intention may include scanning an image, measuring a detected ROI, freezing a screen, editing diagnostic information, and saving the diagnostic information, and may exclude some of the aforementioned actions or add other actions according to various conditions, such as the computing performance of the CAD apparatus 200, the purpose of diagnosis, the target of diagnosis, and the user's proficiency and experience. As described above, when the diagnostic intention corresponds to a probe motion that is determined with reference to the intention-based classification information, the diagnostic intention is determined as the user's diagnostic intention, where the intention-based classification information contains mapping information of probe motions matched to diagnostic intentions.

In operation 716, the CAD apparatus 200 performs a diagnostic procedure that corresponds to the determined user's diagnostic intention. For example, if the user's intention is to measure an ROI because the ROI has been determined to be a lesion, then features of the detected lesion are extracted and a malignancy/benignity classification is performed. If the user's diagnostic intention is to freeze the screen, then the current screen is frozen and the measurement result is displayed thereon. Additionally, if the user's diagnostic intention is to save the diagnostic information, the diagnostic information displayed on the current screen is saved; if the diagnostic intention is to edit the diagnostic information, the current screen is switched to edit mode; if the diagnostic intention is to scan an image, the current screen is initialized and the next input image from the probe is displayed on the screen.

Figure 8:
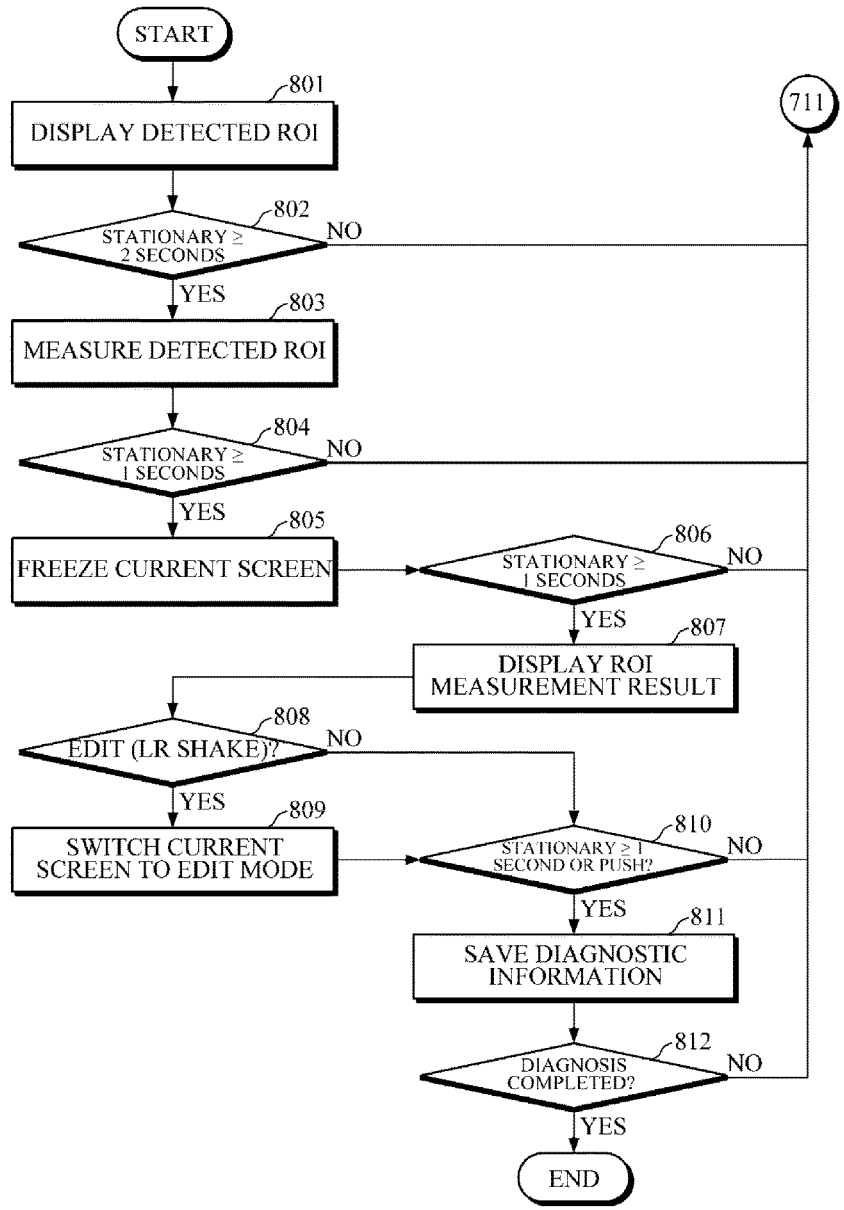
FIG. 8 is a flowchart illustrating a method of performing a diagnostic procedure based on a probe motion in the CAD method of FIG. 7.

FIG. 8 is a flowchart illustrating a method of performing a diagnostic procedure based on a probe motion in the CAD method of FIG. 7. Operation 720 will be described in detail with reference to FIG. 8.

First, if an ROI is detected in operation 713 of FIG. 7, in operation 801, the CAD apparatus 200 displays the detected ROI by marking the detected ROI on the current image on the screen. At this time, by using position or size information of the detected ROI, a visible mark, for example, a bounding box or an oval, or circle mark may be output to indicate the detected ROI.

In operation 802, the CAD apparatus 200 determines whether the probe has been stationary for 2 seconds or more from the moment the ROI was detected. If the CAD apparatus 200 determines that the probe has been stationary for 2 seconds or more, the CAD apparatus 200 determines that the user's diagnostic intention is to measure the ROI, and the CAD apparatus 200 continues in operation 803. If the CAD apparatus 200 determines that the user moves the probe during the 2 seconds, the CAD apparatus 200 determines that the probe motion is a moving motion and that the user's diagnostic intention is to continuously scan an examined area, and the CAD apparatus 200 returns to operation 711 of FIG. 7.

In operation 803, the CAD apparatus 200 measures the detected ROI corresponding to the user's diagnostic intention.

In operation 804, the CAD apparatus 200 determines whether the probe has been stationary for 1 second or more from the moment the ROI measurement started. If the CAD apparatus 200 determines that the probe has been stationary for 1 second more, the CAD apparatus 200 determines that the user's diagnostic intention is to freeze the screen to observe both the current image and the measurement result of the ROI, and the CAD apparatus 200 continues in operation 805. If the CAD apparatus 200 determines that the user moves the probe during the 1 second, the CAD apparatus 200 determines that the user is not interested in the current ROI any longer, and the CAD apparatus 200 returns to operation 711.

In operation 805, the CAD apparatus 200 freezes the current screen.

In operation 806, the CAD apparatus 200 determines whether the probe has been stationary for 1 second or more from the moment the screen was frozen. If the CAD apparatus 200 determines that the probe has been stationary for 1 second more, the CAD apparatus 200 determines that the user's diagnostic intention is to display diagnostic information for further analysis of the diagnostic information, and the CAD apparatus 200 continues in operation 807. If the CAD apparatus 200 determines that the user moves the probe during the 1 second, the CAD apparatus 200 determines that the user's diagnostic intention is to scan an image, and the CAD apparatus 200 returns to operation 711.

In operation 807, the CAD apparatus 200 displays the diagnostic information that contains the ROI measurement result.

Operations 804 to 807 may be combined into two steps: for example, a step in which it is determined whether a probe is stationary for 2 seconds from the moment the ROI measurement started, and a step in which, if the probe motion is stationary for the 2 seconds, the current screen is frozen and the diagnostic information is output.

In operation 808, the CAD apparatus 200 determines whether the probe motion is an editing motion such as a left-right shake. If the CAD apparatus 200 determines that the probe motion is an editing motion, the CAD apparatus 200 determines that the user's diagnostic intention is to edit diagnostic information, and the CAD apparatus 200 continues in operation 809. Otherwise, the CAD apparatus 200 continues in operation 810.

In operation 809, the CAD apparatus 200 switches the current screen to an edit mode.

In operation 810, that the CAD apparatus 200 determines whether the probe has been stationary for 1 second or more after the diagnostic information was displayed or the screen was switched to the edit mode, or whether the probe motion is a saving motion or pushing motion even before the 1 second has elapsed. If the CAD apparatus 200 determines that the probe has been stationary for 1 second or more, or that the probe motion is a pushing motion, the CAD apparatus 200 determines that the user's diagnostic intention is to save diagnostic information, and the CAD apparatus 200 continues in operation 811. If the CAD apparatus 200 determines that the user moves the probe during the 1 second, or that the probe motion is not a pushing motion, the CAD apparatus 200 determines that the user's diagnostic intention is to scan an image, and the CAD apparatus 200 returns to operation 711.

In operation 811, the CAD apparatus 200 saves the diagnostic information that contains the current image, the ROI information, and/or the measurement result of the ROI.

In operation 812, the CAD apparatus 200 determines whether diagnosis has been completed, e.g., whether the user turns off the CAD apparatus 200 or performs a probe motion. If the CAD apparatus 200 determines that the diagnosis has been completed, the CAD apparatus 200 also determines that the user's diagnostic intention is to finish the diagnostic process, and accordingly, the diagnosis is terminated. Otherwise, the CAD apparatus 200 returns to operation 711.

Figure 9:
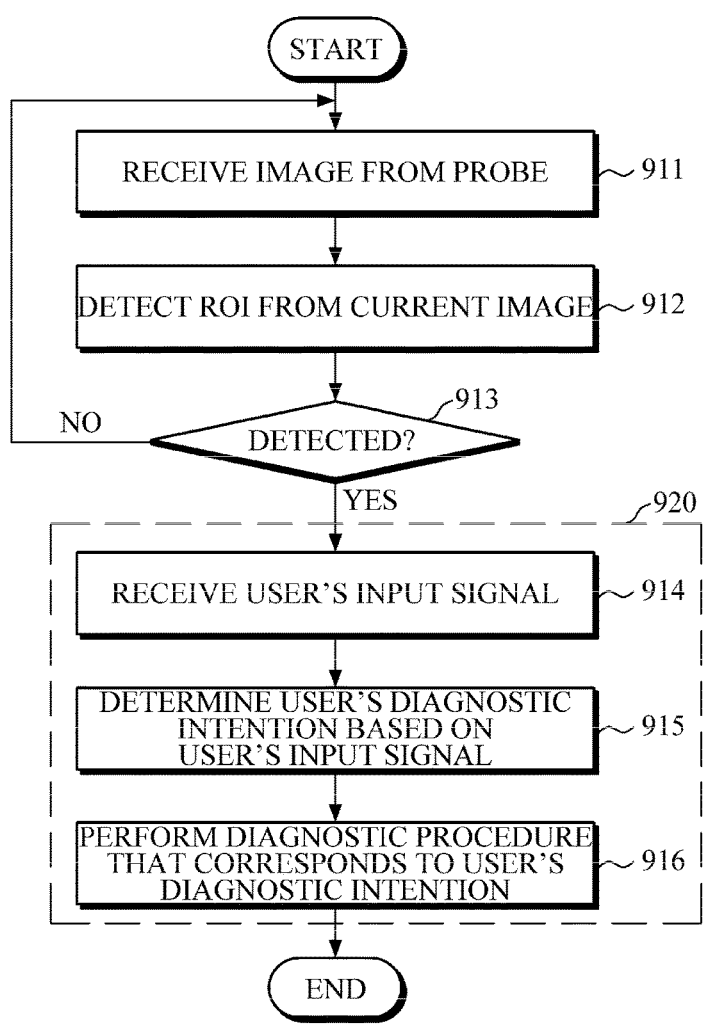
FIG. 9 is a flowchart illustrating a CAD method, according to another exemplary embodiment.

FIG. 9 is a flowchart illustrating a CAD method, according to another exemplary embodiment.

FIG. 9 shows an exemplary embodiment of a diagnostic method performed by the CAD apparatus 500 of FIG. 5 based on an input signal.

In operation 911, the CAD apparatus 500 receives an image from a probe.

In operation 912, the CAD apparatus 500 detects or scans for an ROI from the received current image. At this time, the ROI may be scanned for by applying to the current image any of the various object detection algorithms suitable to computing performance of the CAD apparatus 500.

In operation 913, the CAD apparatus 500 determines whether an ROI is detected from the received current image. If the CAD apparatus 500 determines that an ROI is not detected, the CAD apparatus 500 returns to operation 911 in which the CAD apparatus 500 receives another image from the probe. If the CAD apparatus 500 determines that an ROI is detected, the CAD apparatus 500 continues in operation 914.

In operation 914, the CAD apparatus 500 receives a user's input signal.

In operation 915, the CAD apparatus 500 determines the diagnostic intention of the user based on the user's input signal. At this time, as described above, the user's diagnostic intention may be determined with reference to intention-based classification information that contains diagnostic intentions matched to at least one of the following: the number, type, and combination patterns of the input signals from each input device.

In operation 916, the CAD apparatus 500 performs a diagnostic procedure that corresponds to the determined diagnostic intention of the user.

Figure 10:
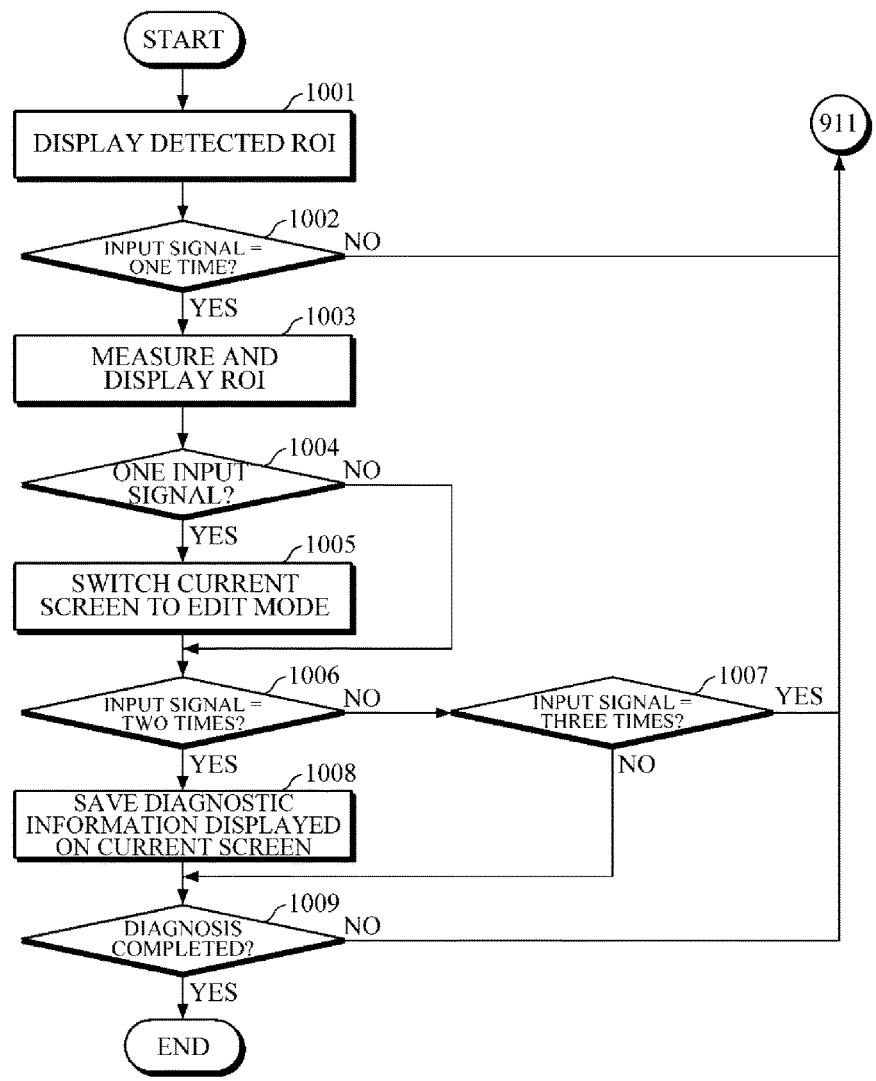
FIG. 10 is a flowchart illustrating a method of performing a diagnostic procedure based on an input signal in the CAD method of FIG. 9.

FIG. 10 is a flowchart illustrating a method of performing a diagnostic procedure based on an input signal in the CAD method of FIG. 9. Operation 920 will be described in detail with reference to FIG. 10.

Referring to FIG. 10, if an ROI is detected in operation 913 of FIG. 9, in operation 1001, the CAD apparatus 500 displays the detected ROI by marking the detected ROI on the current image on the screen. At this time, a colored visible mark (e.g., a bounding box, an oval, or a circle) may be output based on the location or size information of the detected ROI to indicate the detected ROI.

In operation 1002, the CAD apparatus 500 determines whether a single input signal is received within one time unit after the ROI is detected. If the CAD apparatus 500 determines that the input signal is received within the one time unit, the CAD apparatus 500 determines that the user's diagnostic intention is to measure the ROI, and the CAD apparatus 500 continues in operation 1003. If the CAD apparatus 500 determines that the input signal is not received within the one time unit, or that one or more input signals are received consecutively three times within the one time unit, the CAD apparatus 500 determines that the user's diagnostic intention is to scan an image, and the CAD apparatus 500 returns to operation 911 of FIG. 9.

In operation 1003, the CAD apparatus 500 performs the ROI measurement procedure, and displays the diagnostic information that contains the measurement result of the ROI on the screen.

In operation 1004, the CAD apparatus 500 determines whether one or more input signals are received only one time within a time unit after the ROI is displayed. If the CAD apparatus 500 determines that one or more input signals are received only one time within a time unit, the CAD apparatus 500 determines that the user's diagnostic intention is to edit the diagnostic information, and the CAD apparatus 500 continues in operation 1005. Otherwise, the CAD apparatus 500 continues in operation 1006.

In operation 1005, the CAD apparatus 500 switches the current screen to an edit mode.

In operation 1006, the CAD apparatus 500 determines whether one or more input signals are consecutively received two times within a time unit after the ROI is displayed or after the screen is switched to the edit mode. If the CAD apparatus 500 determines that one or more input signals are consecutively received two times within a time unit, the CAD apparatus 500 determines that the user's diagnostic intention is to save the diagnostic information, and the CAD apparatus 500 continues in operation 1008. Otherwise, the CAD apparatus 500 continues in operation 1007.

In operation 1008, the CAD apparatus 500 saves the diagnostic information displayed on the current screen.

In operation 1007, the CAD apparatus 500 determines whether one or more input signals are consecutively received three times within a time unit. If the CAD apparatus 500 determines that one or more input signals are consecutively received three times within a time unit, the CAD apparatus 500 determines that the user's diagnostic intention is to scan an image, and the CAD apparatus 500 returns to operation 911. Otherwise, the CAD apparatus 500 continues in operation 1009.

In operation 1009, the CAD apparatus 500 determines whether diagnosis is completed, e.g., whether the user turns off the CAD apparatus 500 or performs a probe motion. If the CAD apparatus 500 determines that the diagnosis is completed, the CAD apparatus 500 also determines that the user's diagnostic intention is to finish the diagnostic process, and so the diagnosis is terminated. Otherwise, the CAD apparatus 500 returns to operation 911 to repeat the subsequent operations.

While not restricted thereto, an exemplary embodiment can be embodied as computer-readable code on a computer-readable recording medium. For example, a control program that controls the above-described operations of the multi-view display device 100 or 200 may be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses 100, 200 can include circuitry, a processor, a microprocessor, etc., and may execute a computer program stored in a computer-readable medium.

The foregoing exemplary embodiments and advantages are examples and are not to be construed as limiting. The present teaching can be readily applied to other types of apparatuses. Also, the description of exemplary embodiments is intended to be illustrative, and not to limit the scope of the claims, and many alternatives, modifications, and variations will be apparent to those skilled in the art.

What is claimed is:

1. A computer-aided diagnostic (CAD) apparatus comprising:
    a memory configured to store instructions; and
    at least one processor configured to, upon executing the stored instructions:
        detect a region of interest (ROI) from an image input from a probe;
        determine a motion of the probe, matched to a user's manipulation of the probe or a state of the probe, among a plurality of motions of the probe, in response to the ROI being detected;
        determine a diagnostic intention of a user corresponding to the determined motion of the probe, based on mapping information that maps motions of the probe to diagnostic intentions of the user, wherein the mapping information is pre-stored in the memory; and
        perform a diagnostic procedure, based on the determined diagnostic intention of the user.

2. The CAD apparatus of claim 1, wherein the at least one processor is further configured to determine the motion of the probe, based on consecutive images input from the probe.

3. The CAD apparatus of claim 2, wherein the at least one processor is further configured to:
    calculate a similarity between the input consecutive images; and
    determine the motion of the probe, based on the calculated similarity.

4. The CAD apparatus of claim 1, wherein the at least one processor is further configured to determine the motion of the probe, using one or more sensors that are mounted on the probe, the one or more sensors comprising at least one among an acceleration sensor, a gyro sensor, and a motion sensor.

5. The CAD apparatus of claim 1, wherein the diagnostic intention of the user is to perform one among scanning another image with the probe, measuring the ROI, freezing a screen, editing diagnostic information, and saving the diagnostic information.

6. The CAD apparatus of claim 5, wherein the at least one processor is further configured to:
    measure the detected ROI, in response to the diagnostic intention of the user being determined to be to perform measuring the ROI;
    control a display to freeze the screen and display a result of the measuring the ROI on the frozen screen, in response to the diagnostic intention of the user being determined to be to perform freezing the screen; and
    store the diagnostic information that is displayed on the screen, in response to the diagnostic intention of the user being determined to be to perform saving the diagnostic information.

7. The CAD apparatus of claim 6, wherein the at least one processor is further configured to:
    in response to the diagnostic intention of the user being determined to be to perform editing the diagnostic information, control the display to switch the screen to an edit mode; and
    in response to the diagnostic intention being determined to be to perform scanning the other image, control the display to initialize the frozen screen and display the other image input from the probe on the initialized screen.

8. The CAD apparatus of claim 1, wherein the motion of the probe comprises at least one among being stationary, a moving motion, an editing motion, and a saving motion.

9. The CAD apparatus of claim 8, wherein the at least one processor is further configured to determine that the diagnostic intention of the user is to perform measuring the ROI, in response to the motion of the probe being determined to comprise being stationary during a first time unit from a moment the ROI is detected.

10. The CAD apparatus of claim 9, wherein the at least one processor is further configured to determine that the diagnostic intention of the user is to perform freezing a screen, in response to the motion of the probe being determined to comprise being stationary during a second time unit from a moment the ROI is measured.

11. The CAD apparatus of claim 10, wherein the at least one processor is further configured to:
    in response to the motion of the probe being determined to comprise the moving motion within a third time unit from a moment the screen is frozen, determine that the diagnostic intention of the user is to perform scanning another image with the probe; and
    in response to the motion of the probe being determined to comprise being stationary during the third time unit from the moment the screen is frozen, determine that the diagnostic intention of the user is to perform displaying a result of the measuring the ROI on the frozen screen.

12. The CAD apparatus of claim 10, wherein the at least one processor is further configured to:
    in response to the motion of the probe being determined to comprise the editing motion within a third time unit from the moment the screen is frozen, determine that the diagnostic intention of the user is to perform editing diagnostic information; and
    in response to the motion of the probe being determined to comprise the saving motion within the third time unit from the moment the screen is frozen, determine that the diagnostic intention of the user is to perform saving the diagnostic information.

13. A computer-aided diagnostic (CAD) method comprising:
    detecting a region of interest (ROI) from an image input from a probe;
    determining a motion of the probe, matched to a user's manipulation of the probe or a state of the probe, among a plurality of motions of the probe, in response to the ROI being detected;
    determining a diagnostic intention of a user corresponding to the determined motion of the probe, based on mapping information that maps motions of the probe to diagnostic intentions of the user, wherein the mapping information is pre-stored in a memory; and performing a diagnostic procedure, based on the determined diagnostic intention of the user.

14. The CAD method of claim 13, wherein the diagnostic intention of the user is to perform one among scanning another image with the probe, measuring the ROI, freezing a screen, editing diagnostic information, and saving the diagnostic information.

15. The CAD method of claim 14, wherein the performing the diagnostic procedure comprises:

measuring the detected ROI, in response to the diagnostic intention of the user being determined to be to perform measuring the ROI;

freezing the screen and displaying a result of the measuring the ROI on the screen, in response to the diagnostic intention of the user being determined to be to perform freezing the screen; and storing the diagnostic information that is displayed on the screen, in response to the diagnostic intention of the user being determined to be to perform saving the diagnostic information.

16. The CAD method of claim 15, wherein the performing the diagnostic procedure further comprises:

in response to the diagnostic intention of the user being determined to be to perform editing the diagnostic information, switching the screen to an edit mode; and in response to the diagnostic intention being determined to be to perform scanning the other image, initializing the frozen screen and displaying the other image input from the probe on the initialized screen.

17. A computer-aided diagnostic (CAD) apparatus comprising:

a memory configured to store instructions; and at least one processor configured to, upon executing the stored instructions:

detect a region of interest (ROI) from an image input from a probe;

receive one or more input signals from an interface;

determine, based on mapping information that maps a number of input signals during a pre-set time to diagnostic intentions of a user, a diagnostic intention of the user corresponding to a number of the received one or more input signals, wherein the mapping information is pre-stored in the memory; and perform a diagnostic procedure, based on the determined diagnostic intention of the user.

18. The CAD apparatus of claim 17, wherein the at least one processor is further configured to determine the diagnostic intention of the user, based on types of the one or more input signals.

* * * * *